United States Patent [19]

Metcalf et al.

[11] 3,946,060
[45] Mar. 23, 1976

[54] ACETYLENE DERIVATIVES

[75] Inventors: Brian Walter Metcalf, Strasbourg; Michel Jung, Illkirch, both of France

[73] Assignee: Richardson-Merrell Inc., Wilton, Conn.

[22] Filed: Mar. 18, 1975

[21] Appl. No.: 559,545

[52] U.S. Cl.......... 260/448.2 N; 424/184; 260/404; 260/448.2 E
[51] Int. Cl.² ............................................. C07F 7/10
[58] Field of Search ............................ 260/448.2 N

[56] References Cited
UNITED STATES PATENTS

| | | | |
|---|---|---|---|
| 3,210,425 | 10/1965 | Wotiz et al. | 260/448.2 N X |
| 3,665,026 | 5/1972 | Evans | 260/448.2 N X |
| 3,699,140 | 10/1972 | Chandra et al. | 260/448.2 N |
| 3,755,395 | 8/1973 | Bakassian | 260/448.2 N X |
| 3,856,848 | 12/1974 | Smithwick | 260/448.2 N X |

*Primary Examiner*—Paul F. Shaver
*Attorney, Agent, or Firm*—L. Ruth Hattan; Eugene O. Retter; George W. Rauchfuss, Jr.

[57] ABSTRACT

Novel compounds of the following general formula are useful pharmacologic agents and are useful as intermediates for the preparation of pharmacologically useful compounds.

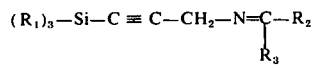

wherein $R_1$ is selected from a lower alkyl group having from 1 to 4 carbon atoms, $R_2$ is selected from hydrogen and phenyl; and $R_3$ is selected from phenyl and trialkylmethyl; and acid addition salts thereof.

2 Claims, No Drawings

ACETYLENE DERIVATIVES

FIELD OF INVENTION

This invention relates to novel acetylene derivatives.

SUMMARY OF INVENTION

Compounds of the following general Formula I are useful as monoamine oxidase inhibitors and are useful as intermediates for the preparation of pharmacologically useful compounds.

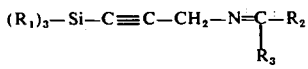

Formula I

In the above general Formula I, $R_1$ is selected from a lower alkyl group having from 1 to 4 carbon atoms; $R_2$ is selected from hydrogen and phenyl; and $R_3$ is selected from phenyl and trialkylmethyl wherein the alkyl moiety contains one or two carbon atoms with the proviso that when $R_3$ is trialkylmethyl, $R_2$ is hydrogen. Acid addition salts of the compounds of general Formula I are also included in this invention.

DETAILED DESCRIPTION OF INVENTION

In the above general Formula I, lower alkyl groups of from 1 to 4 carbon atoms which $R_1$ may be are methyl, ethyl, n-propyl and n-butyl.

In the above general Formula I, the trialkylmethyl groups which $R_3$ may represent are tert-butyl and triethylmethyl.

The compounds of general Formula I are useful as intermediates in the preparation of compounds which may be represented by the following Formula II which compounds are useful as sedatives or γ-aminobutyric acid transaminase inhibitors as described in copending U.S. application Ser. No. 559,597 filed Mar. 18, 1975.

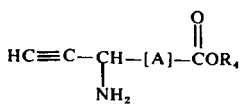

Formula II wherein $R_4$ represents hydroxy, an alkoxy group or an amide function; [A] represents

or —CH=CH— wherein $R_5$ represents hydrogen, a lower alkyl group, phenyl and substituted phenyl; and $n$ is an integer of from 1 to 5.

The compounds of general Formula I are also useful as monoamine oxidase inhibitors rendering them useful in treating mental depression and hypertension.

As pharmacologic agents the compounds of this invention can be administered orally or parenterally to animals, particularly warm blooded animals and mammals, either alone or in the form of pharmaceutical preparations containing as the active ingredient a compound of general Formula I to achieve the desired effect. Pharmaceutical preparations containing compounds of this invention and conventional pharmaceutical carriers can be employed in unit dosage forms, such as, solids, for example, tablets, pills and capsules or liquid solutions, suspensions or elixirs for oral administration, or liquid solutions, suspensions and emulsions for parenteral use. The quantity of compound administered can vary over a wide range to provide from 0.1 to 200 mg/kg (milligram per kilogram) of body weight of the patient per day. Unit doses of these compounds can contain from about 50 to 200 mg of the compound and may be administered, for example, from 1 to 4 times daily.

The preferred compound of this invention is 1-trimethylsilyl-1-propynyl-1-iminobenzyl having the following structure:

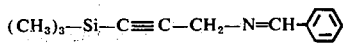

The compounds of this invention may be prepared by the addition of protecting groups on the acetylene function and the nitrogen function of propargylamine. Protection of the nitrogen function of propargylamine is accomplished by forming in a known manner a Schiff's base with a non-enolizable carbonyl bearing carbon, such as benzaldehyde, benzophenone, or trialkylacetaldehyde, specifically 2,2-dimethylpropanal and 2,2-diethylbutanal. Protection of the acetylenic function is accomplished by reacting the above-described Schiff's base with trimethylsilylchloride, triethylsilylchloride or higher trialkylsilyl chloride, forming in a known manner (E. J. Corey and H. A. Kirst, *Tetrahedron Letters*, 1968, 5041) the corresponding trialkylsilyl derivatives.

The following examples are illustrative of the compounds of this invention.

EXAMPLE 1

Propan-1-yne-3-iminobenzyl

A solution of propargylamine (26.1 g, 0.47 M) and benzaldehyde (52 g, 0.49 M) in benzene (150 ml) is treated with $MgSO_4$ (20 g). The reaction mixture is stirred at room temperature for 30 minutes, then filtered. Excess water is removed by way of azeotropic distillation, the solution concentrated, and the residue distilled to give propan-1-yne-3-iminobenzyl (55.5 g, 82%) b.p. 107°–110° C (10 mm Hg).

EXAMPLE 2

1-Trimethylsilyl-1-propynyl-1-iminobenzyl

To a mechanically stirred solution of propan-1-yne-3-iminobenzyl (43.5 g, 0.30 M) in tetrahydrofuran (400 ml) at 0° C is added, during 30 minutes, ethyl magnesium bromide (285 ml of a 1.12 M solution, 0.316 M). After 30 minutes at 0° C, the resulting solution is treated with a solution of trimethylsilylchloride (32.4 g, 0.30 M) in tetrahydrofuran (100 ml), the addition taking 45 minutes. After stirring at 0° C for an additional 1½ hours, the solution is treated with brine. The organic phase is separated and washed with brine (8 × 100 ml), then dried and concentrated on a rotorvapor. The residue is distilled to afford a liquid (52.2 g, 80%) b.p. 92°–110° C, 0.6 mm Hg. An aliquot was redistilled to give 1-trimethylsilyl-1-propynyl-3-iminobenzyl.

Following the procedure of Example 1, only substituting for benzaldehyde an appropriate amount of benzophenone, 2,2-dimethylpropanal or 2,2-diethylbutanal the following respective compounds are obtained:

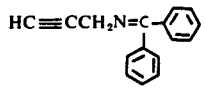

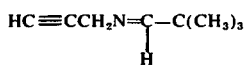

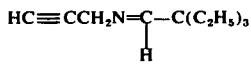

When an appropriate amount of the above amine-protected propargylamine compounds are substituted for propan-1-yne-3-iminobenzyl in the procedure of Example 2, the following respective products are obtained:

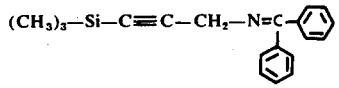

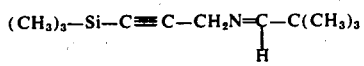

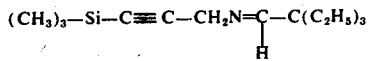

We claim:

1. A compound selected from a base of the formula:

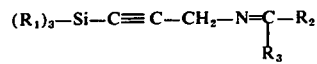

wherein $R_1$ is selected from a lower alkyl group having from 1 to 4 carbon atoms; $R_2$ is selected from hydrogen and phenyl; $R_3$ is selected from phenyl and trialkylmethyl with the proviso that when $R_3$ is trialkylmethyl, $R_2$ is hydrogen; and acid addition salts thereof.

2. A compound of claim 1 which is:

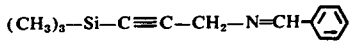

* * * * *

UNITED STATES PATENT AND TRADEMARK OFFICE
CERTIFICATE OF CORRECTION

PATENT NO. : 3,946,060
DATED : March 23, 1976
INVENTOR(S) : Brian W. Metcalf and Michel Jung It is certified that error appears in the above-identified patent and that said Letters Patent are hereby corrected as shown below:

Column 1, line 38 "... Ser. No. 559,597..." should read "... Ser. No. 559,547...".

Signed and Sealed this

First Day of March 1977

[SEAL]

Attest:

RUTH C. MASON
Attesting Officer

C. MARSHALL DANN
Commissioner of Patents and Trademarks